United States Patent
Ichizawa et al.

(10) Patent No.: US 8,483,355 B2
(45) Date of Patent: Jul. 9, 2013

(54) RADIATION INSPECTION APPARATUS COMPRISING A GAS EJECTING UNIT FOR SUPPORTING AND CONVEYING A SHEET-LIKE SAMPLE

(75) Inventors: Yasushi Ichizawa, Musashino (JP); Hirohiko Obinata, Musashino (JP)

(73) Assignee: Yokogawa Electric Corporation, Musashino-Shi, Tokyo (JP)

( * ) Notice: Subject to any disclaimer, the term of this patent is extended or adjusted under 35 U.S.C. 154(b) by 279 days.

(21) Appl. No.: 12/879,274

(22) Filed: Sep. 10, 2010

(65) Prior Publication Data
US 2011/0069813 A1 Mar. 24, 2011

(30) Foreign Application Priority Data
Sep. 24, 2009 (JP) ................. 2009-218975

(51) Int. Cl.
*G01N 23/083* (2006.01)
(52) U.S. Cl.
USPC .................. 378/54; 378/53; 378/58
(58) Field of Classification Search
USPC ................. 378/53, 54, 55, 56, 58
See application file for complete search history.

(56) References Cited

U.S. PATENT DOCUMENTS

| | | | |
|---|---|---|---|
| 4,266,142 A | | 5/1981 | Crawford |
| 4,271,601 A | * | 6/1981 | Koponen et al. ............... 34/641 |
| 4,472,888 A | | 9/1984 | Spiller |
| 4,767,042 A | | 8/1988 | Daane |
| 5,014,288 A | * | 5/1991 | Chase et al. .................... 378/53 |
| 5,418,830 A | * | 5/1995 | Florent ........................... 378/89 |
| 5,518,360 A | * | 5/1996 | Toda et al. ..................... 414/755 |
| 6,377,652 B1 | * | 4/2002 | Sturm ............................. 378/53 |
| 6,421,415 B1 | * | 7/2002 | Peczkis et al. ................. 378/46 |
| 6,600,805 B2 | * | 7/2003 | Hansen ........................... 378/53 |
| 6,810,297 B2 | * | 10/2004 | Adin et al. ..................... 700/110 |
| 7,116,750 B1 | * | 10/2006 | Iaquinta et al. ................. 378/53 |
| 7,376,215 B2 | * | 5/2008 | Hofman .......................... 378/53 |
| 7,874,261 B2 | * | 1/2011 | Yamasaki et al. ............. 118/500 |
| 7,905,195 B2 | * | 3/2011 | Yamasaki et al. ............. 118/300 |
| 8,101,047 B2 | * | 1/2012 | Kulma et al. ............... 162/181.2 |
| 2003/0075293 A1 | | 4/2003 | Moeller et al. |

FOREIGN PATENT DOCUMENTS

| | | |
|---|---|---|
| CA | 1 202 431 A1 | 3/1986 |
| CN | 101054930 A | 10/2007 |
| EP | 0 628 808 A1 | 12/1994 |

(Continued)

OTHER PUBLICATIONS

Japanese Office Action dated Jun. 14, 2011, issued in corresponding Japanese Patent Application No. 2009-218975.

(Continued)

*Primary Examiner* — Allen C. Ho
(74) *Attorney, Agent, or Firm* — Westerman, Hattori, Daniels & Adrian, LLP

(57) ABSTRACT

A radiation inspection apparatus includes a conveying unit configured to convey a sheet-like sample, a radiation source configured to emit radiation to the sheet-like sample, a line sensor configured to measure a physical property of the sheet-like sample, the liner sensor disposed to be opposed to the radiation source across the sheet-like sample, and a gas ejecting unit configured to eject gas to the sheet-like sample to reduce vertical conveyance swinging produced by a tension of the sheet-like sample, the gas ejecting unit placed in close proximity to at least one side face of the line sensor.

4 Claims, 9 Drawing Sheets

FOREIGN PATENT DOCUMENTS

| | | |
|---|---|---|
| JP | 63-200731 U | 12/1988 |
| JP | 63-311079 A | 12/1988 |
| JP | 02-293645 A | 12/1990 |
| JP | 11-349179 A | 12/1999 |
| JP | 2002-181714 A | 6/2002 |
| JP | 2004-284751 A | 10/2004 |
| JP | 2006-290504 A | 10/2006 |
| JP | 2009-092657 A | 4/2009 |

OTHER PUBLICATIONS

Chinese Office Action dated Dec. 19, 2011, issued in corresponding Chinese Patent Application No. 201010282677.0.

European Search Report dated Dec. 14, 2010, issued in corresponding European Patent Application No. 10176498.3.

\* cited by examiner though the sample. FIG. 9A is a perspective view, and FIG. 9B is a sectional diagram.

RADIATION INSPECTION APPARATUS COMPRISING A GAS EJECTING UNIT FOR SUPPORTING AND CONVEYING A SHEET-LIKE SAMPLE

TECHNICAL FIELD

The present disclosure relates to a radiation (such as an X-ray, a beta ray, or a gamma ray) inspection apparatus. More particularly, the present disclosure relates to a radiation inspection apparatus which is suitably used in a production step (such as application, edging, surface modification, coating, or drying) of drawing out a sheet-like sample (hereinafter, referred to merely as a sample) from a material roll, and adding a function to the sample.

RELATED ART

In the case where the film thickness of a highly functional sheet such as a thin film sheet or an electrode sheet for a battery is to be measured, usually, the film thickness of a finished product is measured, and the product is distinguished as a good product or a defective product as required, and then wound around a finished product roll. Also immediately after material loading, or in each value-added step, the inspection of the film thickness may be performed as required.

FIGS. 9A and 9B show a related-art radiation inspection apparatus in which thickness measurement and defect inspection are performed while the interval between the radiation source and a sample is kept constant by maintaining constant the position of the conveyance height (hereinafter, such a position is referred to as a pass line) of the sample, thereby causing a constant radiation dose to be transmitted through the sample. FIG. 9A is a perspective view, and FIG. 9B is a sectional diagram.

In FIGS. 9A and 9B, a sample 1 which is wound around a material roll 2, and which is to be subjected to surface modification is passed through an application step performed by an application apparatus 3, and a drying step performed by a drying apparatus 4, and then conveyed by conveyance rollers 7 (see FIG. 9B) to be taken up by a take-up roll 2a.

In the illustrated example, a radiation (for example, an X-ray) source 5 is placed above the subsequent stage of the drying apparatus 4, the radiation radiated from the radiation source 5 passes through the sample 1, and then enters an X-ray line sensor (hereinafter, referred to merely as a line sensor) 6 having a scintillator which is formed to have a width that is substantially equal to that of the sample 1. The line sensor 6 inspects the entire width of the sample 1 for the thickness, a defect, and the like.

[Patent Reference 1] JP-A-63-311079
[Patent Reference 2] JP-A-11-349179
[Patent Reference 3] JP-A-2004-284751

As shown in FIGS. 9A and 9B, the radiation source 5 emits radiation from a point source, and the radiation is transmitted through the sample 1 to be detected by the line sensor 6 which is below the sample. When the sample 1 passes through a position which is closer to the radiation source 5 (the broken line U shown in FIGS. 9A and 9B), the irradiated dose per unit area is larger, and, when the sample passes through a position which is remoter from the radiation source (the broken line D shown in FIGS. 9A and 9B), the dose is smaller.

In the configuration shown in FIGS. 9A and 9B, it is seemed that, in the case where the interval between the take-up roll 2a and the conveyance rollers 7 is large, the sample 1 may be caused to vertically move by the conveyance tension of the sample 1. In the thickness measurement, there is a problem in that the movement of the sample 1 impairs the accuracy.

It is assumed that the distance between the sample 1 and the radiation source 5 is 400 mm, the width of the sample (=sheet width) is 400 mm, and the sample 1 is conveyed in a range where the upward movement is 5 mm and the downward movement is 5 mm. In this case, the irradiation angle (full angle) at the constant position where the sample 1 is stably conveyed is 53.13 degrees, that when the sample is in the upper side is 53.7 degrees, and that when the sample is in the lower side is 52.56 degrees.

Since the angle ratio is equal to the irradiation dose ratio, +1.1% is attained when the sample is in the upper side, and −1.1% is attained when the sample is in the lower side. In the thickness measurement, unlike determination based on a relative contrast, the transmittance of an X-ray is converted to the thickness. Therefore, the measurement accuracy includes the error of plus and minus 1.1%.

Because of the situation where the sample 1 is conveyed while swinging, the line sensor 6 must be disposed while being separated from the sample 1 (as indicated by B, swing width of the sample 1 is large, and thus, the liner sensor 6 must be sufficiently separated so as not to contact with the sample 1 as indicated A). There is a problem in that, with respect to radiation of a low energy region where atmospheric absorption is problematic, the measurement sensitivity is impaired. As the line sensor 6 is disposed closer, generally, influences of the temperature, the humidity, and the atmospheric pressure can be further reduced.

SUMMARY

Exemplary embodiments of the present invention provide an inspection apparatus in which vertical conveyance swinging of a sample is reduced to allow thickness measurement and defect inspection to be performed while maintaining constant the interval between the radiation source 5 and the sample 1, thereby causing a constant radiation dose to be transmitted through the sample, with the result that highly accurate film thickness measurement and defect measurement are enabled.

(1) A radiation inspection apparatus according to an exemplary embodiment of the invention, comprises:
a conveying unit configured to convey a sheet-like sample;
a radiation source configured to emit radiation to the sheet-like sample;
a line sensor configured to measure a physical property of the sheet-like sample, the liner sensor disposed to be opposed to the radiation source across the sheet-like sample; and
a gas ejecting unit configured to eject gas to the sheet-like sample to reduce vertical conveyance swinging produced by a tension of the sheet-like sample, the gas ejecting unit placed in close proximity to at least one side face of the line sensor.

(2) In the radiation inspection apparatus as mentioned in (1), the gas ejecting unit comprises a plurality of nozzles or holes which eject the gas, the plurality of nozzles or holes arranged in plurality of rows in a width direction of the sheet-like sample.

(3) In the radiation inspection apparatus as mentioned in (1) or (2), the gas ejecting unit comprises an eave-like fluid guide formed on a gas ejection port.

(4) In the radiation inspection apparatus as mentioned in (2) or (3), the gas ejecting unit comprises a plurality of suction holes disposed along the nozzles or holes of the gas ejecting unit.

(5) In the radiation inspection apparatus as mentioned in any one of (2) to (4), the line sensor is disposed in a state that an upper face of the liner sensor is slightly lower than the nozzles or holes of the gas ejecting unit.

(6) In the radiation inspection apparatus as mentioned in any one of (2) to (5), the nozzles or holes of the gas ejecting unit includes a first group of nozzles or holes and a second group of nozzles or holes opposed to the first group across the line sensor. Further, the first group of nozzles or holes are configured to eject the gas in a direction inclined against a flow of the sheet-like sample to produce a drag force, and the second group of nozzles or holes are configured to eject the gas in a direction opposite to the ejecting direction of the first group of nozzles or holes against the flow of the sheet-like sample to produce a thrust force (7) The radiation inspection apparatus as mentioned in any one of (1) to (6), further comprises:

a displacement meter configured to measure vertical conveyance swinging of the sheet-like sample; and a controller configured to control an ejection volume of the gas from the nozzles or holes of the gas ejecting unit to reduce vertical conveyance swinging of the sheet-like sample on the basis of a measured value of the displacement meter.

According to the exemplary embodiments, the following effects are attained:

According to (1) to (7), the followings are attained:

1. The distance between the sample and the radiation source, which may be changed in accordance with the tension of the sample, can be always kept constant, and accurate measurement which is free from variation of a radiation dose that is caused by distance variation is enabled.

2. Even in sample conveyance where the tension is low and the span of driving rollers is long, the swing width of the sample can be suppressed.

3. Stable measurement is enabled irrespective of accuracy of the tension control in the production line.

4. The interval between the X-ray line sensor and the sample can be reduced, and influences of the atmospheric pressure, and changes of the temperature, the humidity, and the atmospheric pressure can be further reduced, thereby enabling the measurement sensitivity to be improved.

5. While adherence or deposition of dust is prevented from occurring in the detecting portion of an X-ray line sensor, by performing air purge, it is not necessary to perform dedicated air purge because the gas ejecting unit is adjacently disposed.

6. Both the X-ray line sensor and the gas ejecting unit are commercially available, and hence the system can be easily configured.

Other features and advantages may be apparent from the following detailed description, the accompanying drawings and the claims.

DETAILED DESCRIPTION

Figure 1:
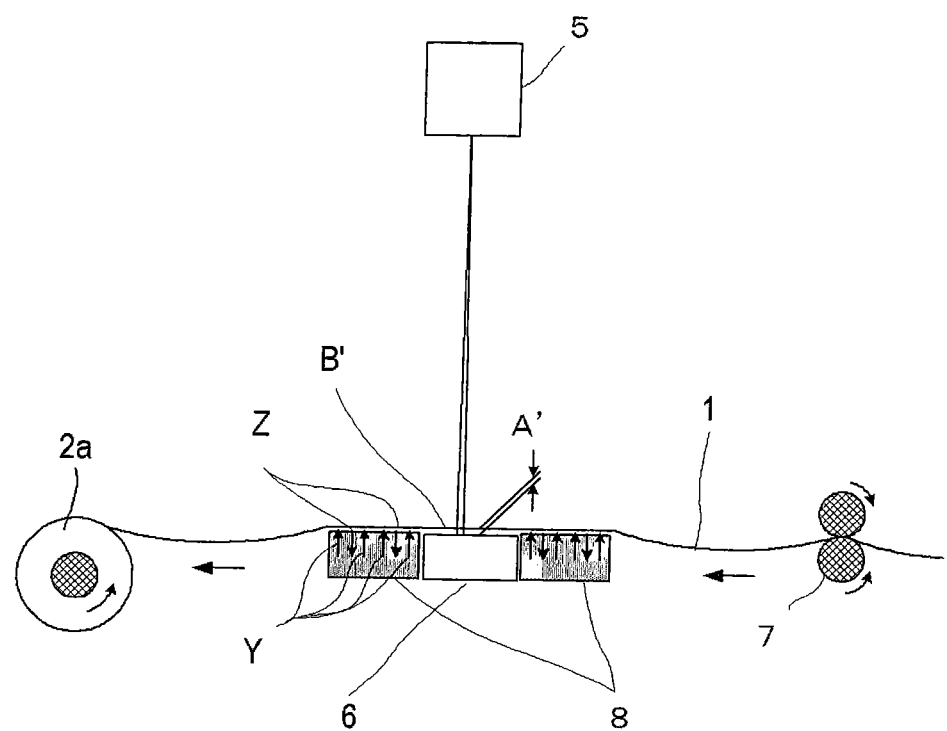
FIG. 1 is a sectional diagram showing a radiation inspection apparatus according to a first embodiment of the invention.
Figure 9A:
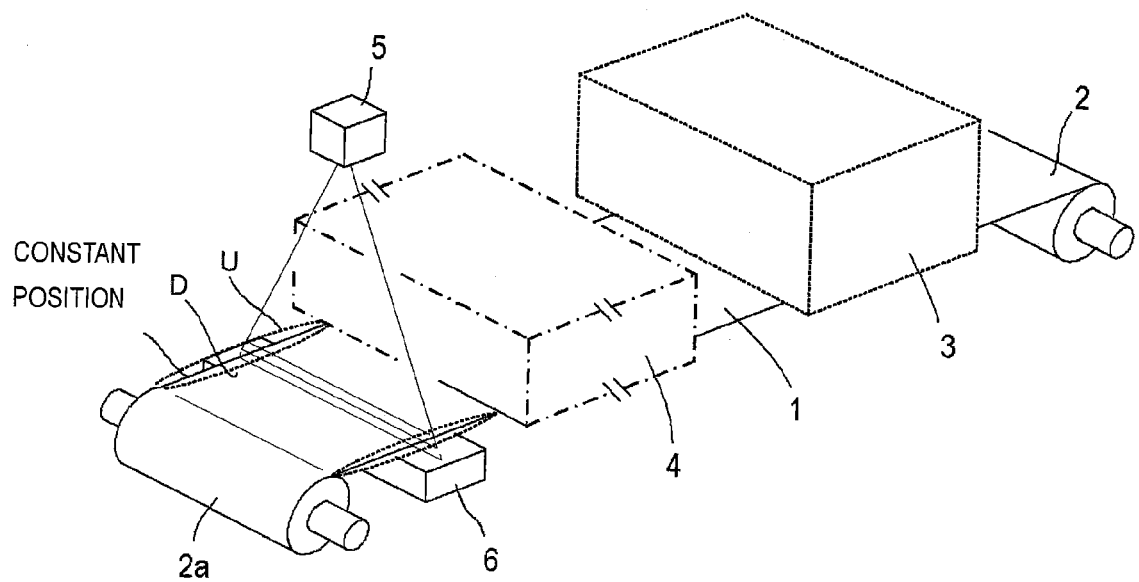
FIG. 9A is a perspective view showing a related-art radiation inspection apparatus.
Figure 9B:
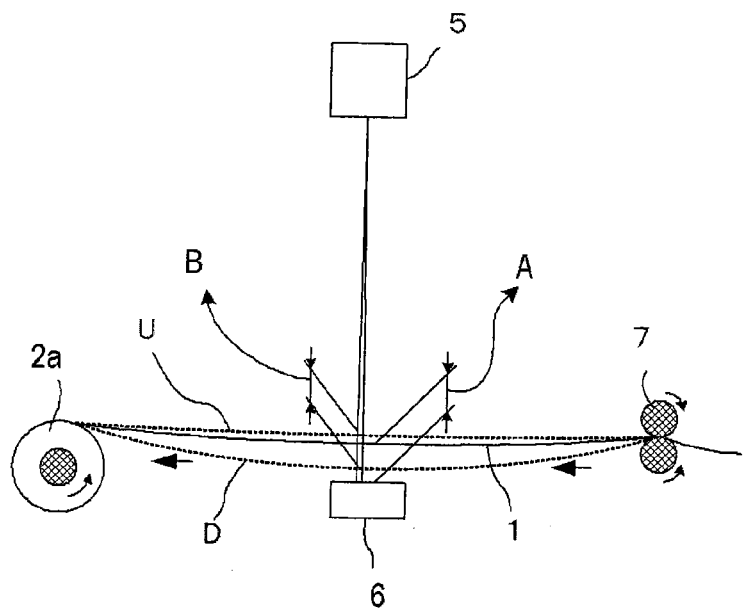
FIG. 9B is a sectional diagram showing the related-art radiation inspection apparatus.

Hereinafter, exemplary embodiments will be described in detail with reference to the drawings. FIG. 1 is a sectional diagram showing a radiation inspection apparatus according to a first embodiment of the invention. The components which are identical with those of FIGS. 9A and 9B are denoted by the same reference numerals.

Referring to FIG. 1, the measurement line sensor 6 having a scintillator is directly opposed to the radiation (X-ray) source 5, and the sample 1 is placed at a position which is remote from the X-ray source 5, and which is in the vicinity of the line sensor 6. When the sample is moved in a direction (in the figure, horizontal) which is substantially perpendicular to the radiation, and detected by the line sensor 6, measurement (inspection) of the sample is enabled.

In FIG. 1, the X-ray line sensor 6 having a scintillator is disposed at a position which is directly opposed to the X-ray source, and the sample flows above and relatively in the vicinity of the X-ray line sensor 6. Gas (air) ejecting units 8 are placed in close proximity to the both sides of the X-ray line sensor 6. The upper face of the X-ray line sensor 6 is placed at a position which is slightly lower than the upper faces of the gas ejecting units 8. The gas ejecting units 8 are disposed so as to be wider than the width of the sample and equivalent to the width (in the longitudinal direction) of the X-ray line sensor 6. Many air ejection holes or ejection nozzles which are indicated by the arrows Y are disposed along the width of the X-ray line sensor 6.

The gas ejecting units 8 are disposed below the sample 1, and configured by minute ejection nozzles or minute holes (not shown) which are disposed in a chamber structure, and the gas is ejected therefrom toward the upper side (sample). In this case, the ejection volume is not sufficient for blowing up the sample. The ejection volume and the flow rate are approximately equal to those of an air bearing which can perform non-contact conveyance, and are used for supporting the weight of the sample.

The conveyance velocity of the sample is controlled by the conveyance rollers 7 in the production line.

The sample is a thin sheet which is relatively light in weight. When the ejection holes are large and their pitches are large, therefore, the sample is partially lifted to become wrinkled. Consequently, the ejection holes are made as small as possible, and their pitch is set to be very small.

Preferably, the structure is configured only by ejection holes which have an ejection volume and ejection port that are adequate for attracting the sheet-like sample 1 while maintaining the non-contacting state by Bernoulli's theorem.

In the gas ejecting units shown in FIG. 1, suction holes indicated by the arrows Z are disposed in addition to the ejection holes indicated by the arrows Y, and the wind force due to the ejection holes, and the attractive force due to the suction holes are controlled by a controller (not shown), whereby the sample 1 is kept at an ideal position. According to the configuration, as compared with the case where a gas is simply ejected, the upper portion of the X-ray line sensor 6, and the sample 1 can be maintained at a narrow interval indicated by A', and the swing width of the sample can be made substantially zero as indicated by B'.

Figure 2:
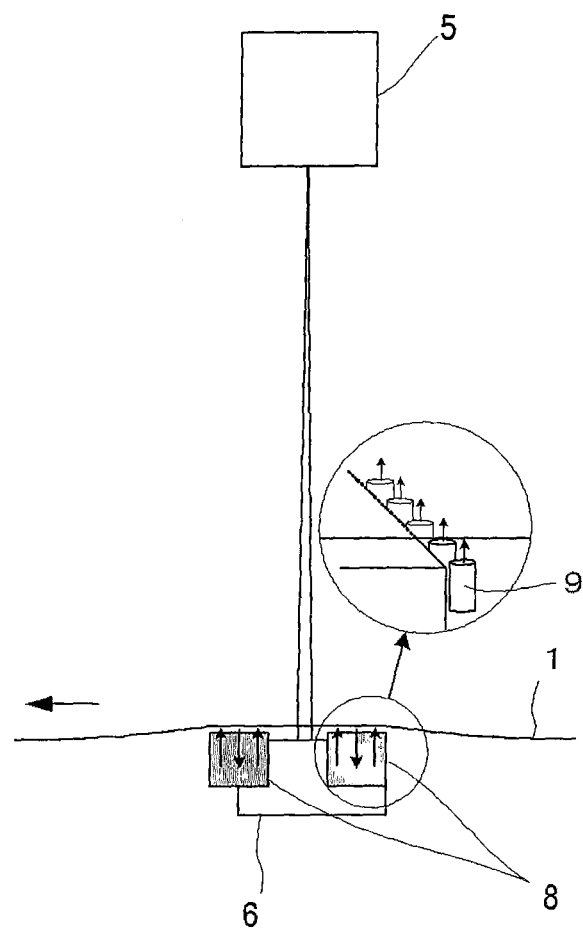
FIG. 2 is a sectional diagram showing a radiation inspection apparatus according to a second embodiment of the invention.

FIG. 2 shows a radiation inspection apparatus according to a second embodiment in which the X-ray line sensor 6 and the gas ejecting units 8 are integrated with each other. Their functions are identical with those shown in FIG. 1.

According to the configuration shown in FIG. 2, adjustments of the positions of the X-ray line sensor 6 and the gas ejecting units 8, and the like are not necessary, and miniaturization is enabled. In the case where the X-ray line sensor 6 and the gas ejecting units 8 are integrated with each other, individual ejection nozzles 9 may be linearly disposed, or a slit (not shown) may be disposed so as to eject the gas toward the sample 1 in the manner of an air curtain. In this case, the slit may not be a simple slit, and the tip end of the slit may be narrowed to increase the flow rate, so that the air ejection volume can be reduced.

Figure 3:
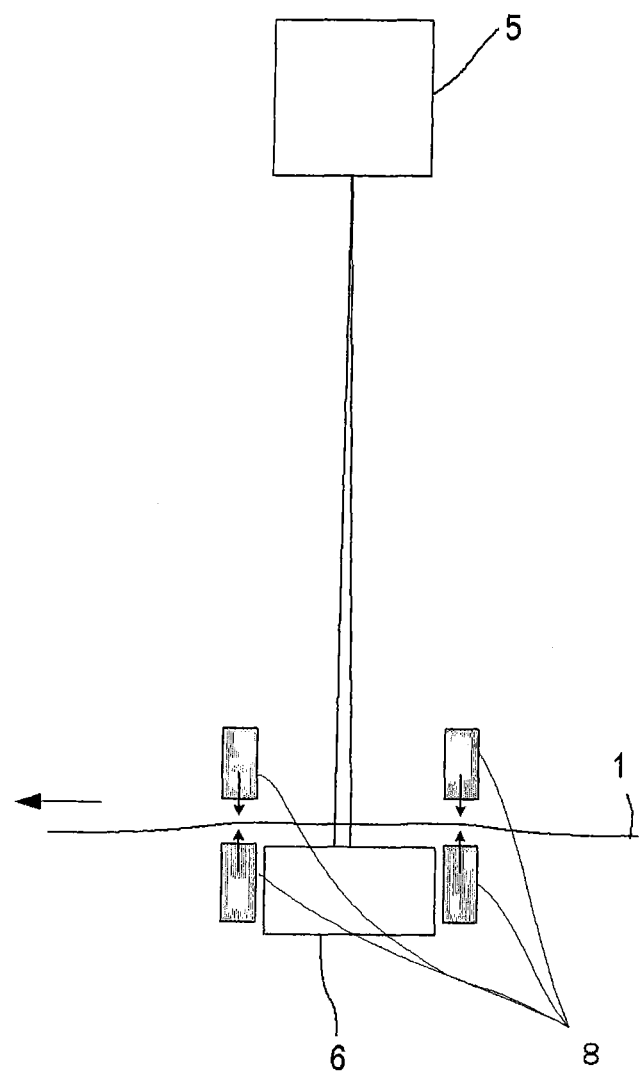
FIG. 3 is a sectional diagram showing a radiation inspection apparatus according to a third embodiment of the invention.

FIG. 3 shows a radiation inspection apparatus according to a third embodiment in which the gas ejecting units 8 are disposed also above the sample 1. Namely, the gas ejecting units 8 are disposed at positions which are on the upstream and downstream sides of the X-ray line sensor 6, respectively, and which are opposed to each other across the sample. The gas is ejected perpendicularly to the sample. Also in the case, the ejection nozzles may be linearly arranged, configured so as to have a slit-like opening, or configured by linearly arranging minute holes.

In this case, however, the ejection nozzles (holes) must be positioned to be correctly opposed so as not to generate a momentum. In the case where, even when the ejection nozzles (holes) are correctly positioned, a momentum is generated, balance adjustment is performed while considering the state of the gas ejection.

When the gas is ejected from the upper and lower sides in this way, the conveyance is further hardly affected by variation of the tension of the sample.

Figure 4:
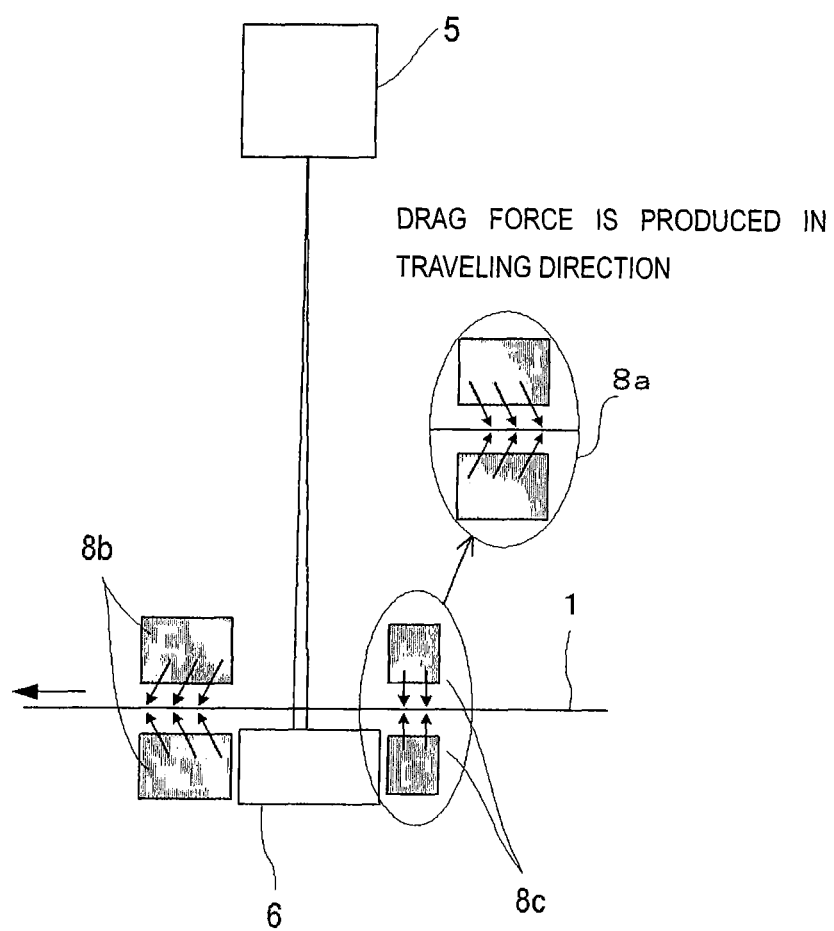
FIG. 4 is a sectional diagram showing a radiation inspection apparatus according to a fourth embodiment of the invention.

FIG. 4 shows a radiation inspection apparatus according to a fourth embodiment in which the ejection direction of the gas is not vertical but inclined. Namely, upstream (front) gas ejecting units 8a are placed while the ejection direction is rightward directed with respect to the conveyance direction of the sample so as to produce a drag (brake) force. By contrast, downstream (rear) gas ejecting units 8b are placed while the ejection direction is leftward directed with respect to the conveyance direction of the sample 1 so as to produce a thrust (acceleration) force. For example, in a case where the gas ejecting units 8a, 8b have a plurality of ejecting nozzles, respectively, the ejecting nozzles of the upstream gas ejecting units 8a are placed in a state that they are inclined with a certain angle with respect to the conveyance direction of the sample so as to produce a drag (brake) force. By contrast, the ejection nozzles of the downstream gas ejecting units 8b are placed in a state that they are inclined with a certain angle in a direction opposite to the inclined direction of the ejecting nozzles of the upstream gas ejecting units 8a with respect to the conveyance direction of the sample 1 so as to produce a thrust (acceleration) force.

Both the drag force and the thrust force are not a large force which may affect the driving of the production line, but a small lateral tension is generated in the sample 1 on the X-ray line sensor 6. Therefore, conveyance in which wrinkle are more hardly caused is enabled.

As shown in FIG. 4, the upstream gas ejecting units 8c may vertically eject the gas.

Alternatively, the downstream gas ejecting units 8b may vertically eject the gas, and the upstream (front) gas ejecting units 8a may be placed while the ejection direction is rightward directed with respect to the conveyance direction of the sample so as to produce a drag (brake) force. Vectors may exist so that a tension is applied in the width direction of the sheet (the direction perpendicular to the sheet conveyance direction).

Figure 5:
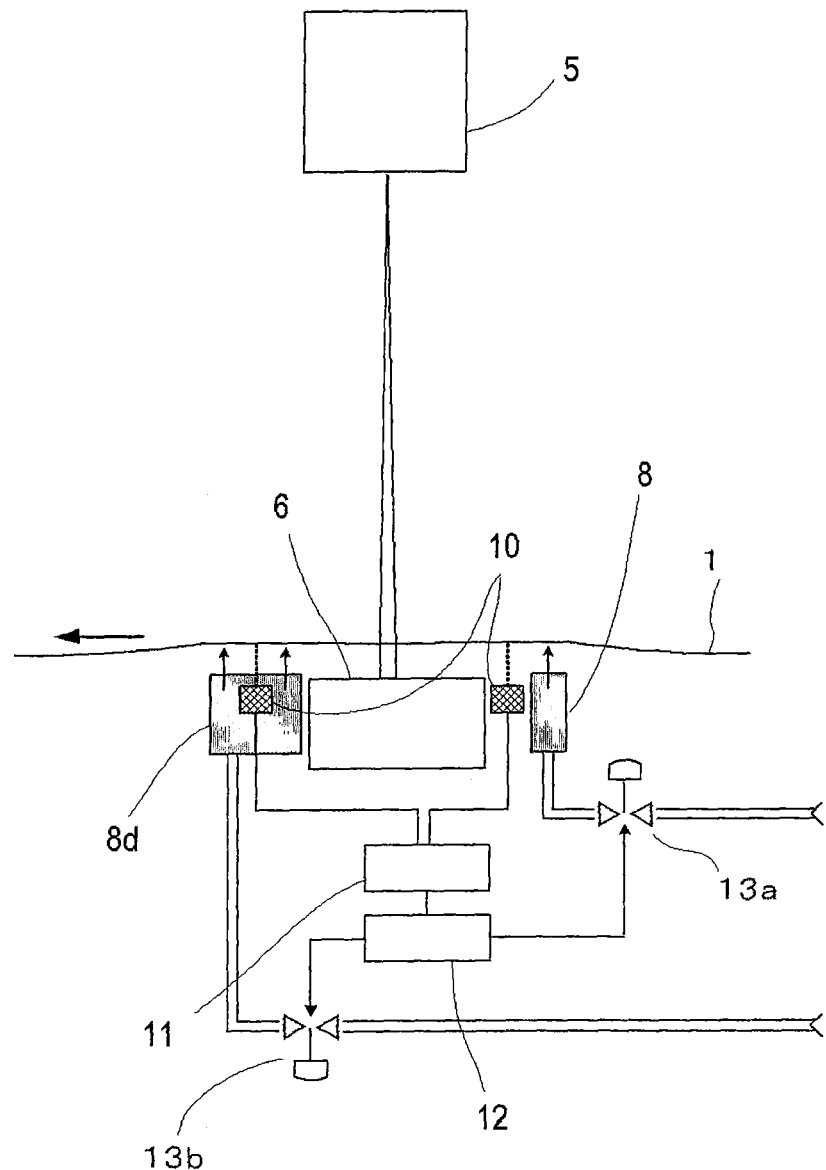
FIG. 5 is a block diagram showing a radiation inspection apparatus according to a fifth embodiment of the invention.

FIG. 5 shows a radiation inspection apparatus according to a fifth embodiment in which displacement meters (including a distance meter and a length meter) 10 which are typified by the laser type or the capacitance type are disposed in the vicinity of the X-ray line sensor 6, and the flow rate or pressure of the ejected gas is feedback controlled, whereby the interval between the sample 1 and the X-ray line sensor 6 is optimally controlled. The displacement meter may be incorporated in gas ejecting units 8d, or juxtaposed with the gas ejecting units 8.

Referring to FIG. 5, the outputs of the displacement meters 10 are measured by a measurement sensor 11, and the measured values are sent to a controller 12. The controller 12 calculates the valve opening so that the interval between the sample 1 and the X-ray line sensor 6 is a predetermined optimum value, and controls control valves 13a, 13b based on the calculated valve opening.

Figure 6:
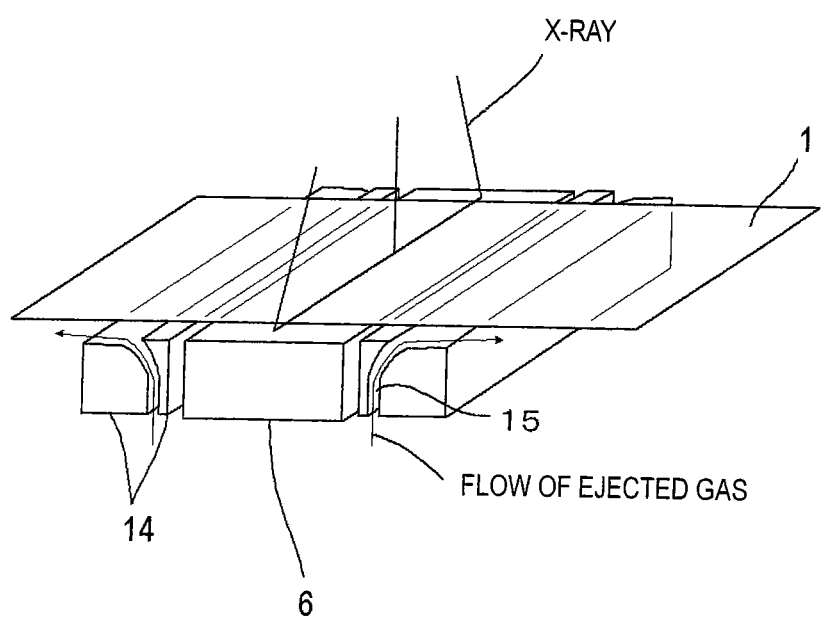
FIG. 6 is a perspective view showing a main part of a radiation inspection apparatus according to a sixth embodiment of the invention.

FIG. 6 shows a radiation inspection apparatus according to a sixth embodiment in which eave-like fluid guides 14 that enhance the Coanda effect of the gas flowing between the X-ray line sensor 6 and the sample 1 are disposed. The distance between the sample 1 and the line sensor 6 can be stabilized by the Coanda effect in which directions of gas flows ejected from slits 15 along the fluid guides 14 are changed.

Figure 7:
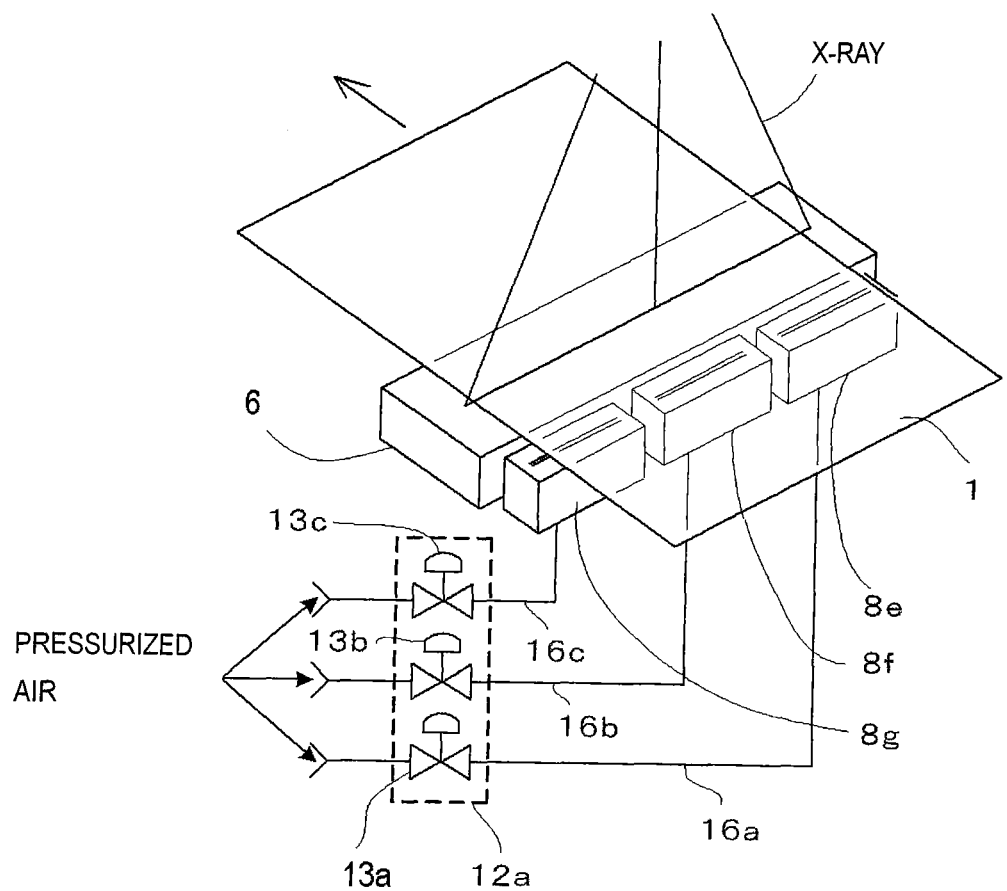
FIG. 7 is perspective view showing a main part of a radiation inspection apparatus according to a seventh embodiment of the invention.

FIG. 7 shows a radiation inspection apparatus according to a seventh embodiment in which the gas ejecting units 8 are divided into a plurality of portions (in the figure, three portions 8e, 8f, 8g). Each of the gas ejecting units is provided with a control valve 13a, 13b, or 13c included in a controller 12a through an air pipe 16a, 16a, or 16c. When the control valves are individually controlled, pressurized air is given to the sample.

According to the configuration, the flow rates and number of the gas ejecting units can be selected in accordance with the size of the width of the sample, and hence it is possible to reduce the cost for ejecting air.

Figure 8:
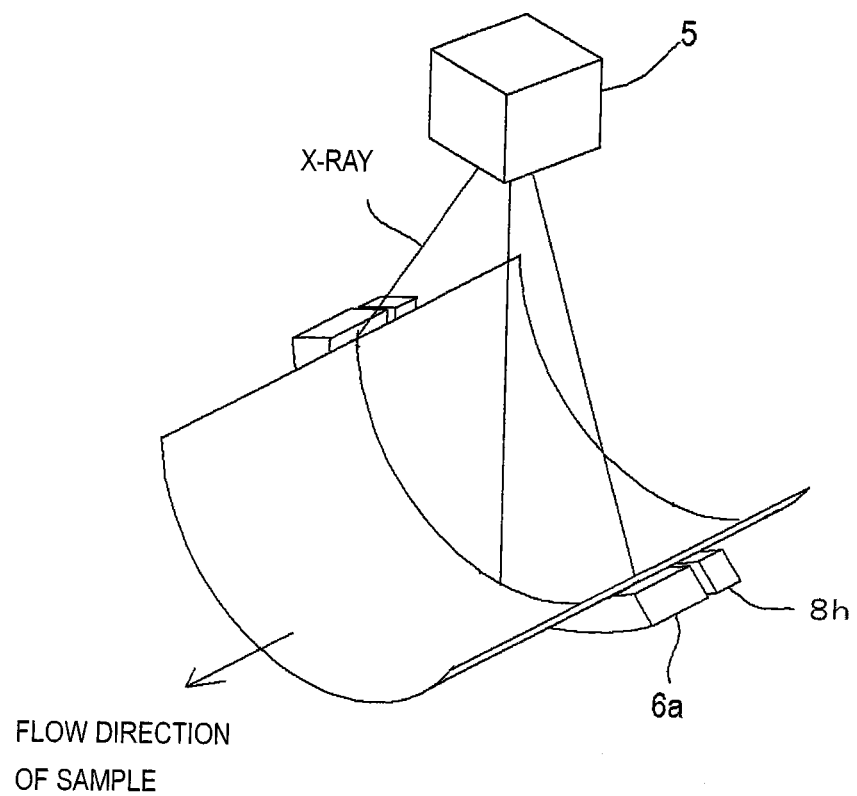
FIG. 8 is perspective view showing a main part of a radiation inspection apparatus according to an eighth embodiment of the invention.

FIG. 8 shows a radiation inspection apparatus according to an eighth embodiment in which the X-ray line sensor 6a is formed into an arcuate shape so that the intensity of the X-ray irradiated from the X-ray source 5 to the sample is uniform, and an air ejecting unit 8h is formed in accordance with the arcuate shape.

According to the configuration, the intensity of the X-ray irradiated from the X-ray source 5 to the sample can be made uniform, and it is not required to perform the X-ray intensity correction which is necessary in the case where the X-ray line sensor 6a is flat.

In the above description, the specific and preferred embodiments are merely shown for the purposes of description and illustration of the invention. In the embodiments, an X-ray is used as the radiation source. Alternatively, for example, a beta ray, or a gamma ray may be used. The gas ejecting units may eject dry air, and include a dedicated filter which filters minute dust, oil mist, excess water, etc. The positions of the gas ejecting units which are adjacently disposed are not limited to the side below the sample, and may be adjacent positions including the upper side so that the sheet is attracted by a negative pressure generated by the flow rate of the ejected gas.

Although not illustrated in FIGS. 2 to 8, in the embodiments, the upper face of the X-ray line sensor may be placed at a position which is slightly lower than the upper faces of the gas ejecting unit.

Therefore, the invention is not limited to the embodiments, and includes Varius changes and modifications without departing the substance of the invention.

What is claimed is:

1. A radiation inspection apparatus comprising:
    a sheet-like sample to be conveyed while its predetermined tension is maintained by a conveyance roller and a take-up roll;
    a radiation source and a line sensor which are disposed to be opposed to each other with the sheet-like sample sandwiched therebetween and measure a physical property of the sheet-like sample;
    a gas ejecting unit which is placed in close proximity to at least one side face of the line sensor and functions as air bearing,
    wherein the gas ejecting unit comprises a plurality of ejecting nozzles or ejecting holes which eject a gas and are arranged in a plurality of rows in a width direction of the sheet-like sample in order to reduce a vertical conveyance swinging produced by variation of the tension of the sheet-like sample, and comprises a plurality of suction units which are disposed along the plurality of ejecting nozzles or ejecting holes and have pressure by which the sheet-like sample is not in contact with the line sensor, and
    wherein the plurality of ejecting nozzles or ejecting holes of the gas ejecting unit are placed in a state that an ejecting direction of the gas from a portion of the plurality of ejecting nozzles or ejecting holes at an upstream side is set in a direction inclined against a flow of the sheet-like sample to produce a drag force, and an ejecting direction of the gas from a portion of the plurality of ejecting nozzles or ejecting holes at a downstream side is set in a direction opposite to the ejecting direction at the upstream side against the flow of the sheet-like sample to produce a thrust force.

2. The radiation inspection apparatus according to claim 1, wherein the line sensor is disposed to be slightly lower than the plurality of ejecting nozzles or ejecting holes of the gas ejecting unit.

3. The radiation inspection apparatus according to claim 2, comprising:
    a displacement meter which measures a vertical displacement of the sheet-like sample from the displacement meter,
    wherein an ejection volume of the gas from the plurality of ejecting nozzles or ejecting holes of the gas ejecting unit can be controlled to reduce the vertical conveyance swinging of the sheet-like sample on the basis of a measured value of the displacement meter.

4. The radiation inspection apparatus according to claim 1, comprising:
    a displacement meter which measures a vertical displacement of the sheet-like sample from the displacement meter,
    wherein an ejection volume of the gas from the plurality of ejecting nozzles or ejecting holes of the gas ejecting unit can be controlled to reduce the vertical conveyance swinging of the sheet-like sample on the basis of a measured value of the displacement meter.

* * * * *